United States Patent [19]
Dorisio Deininger et al.

[11] Patent Number: 6,074,539
[45] Date of Patent: Jun. 13, 2000

[54] ELECTROCHEMICAL SENSOR FOR THE DETECTION OF HYDROGEN CYANIDE

[75] Inventors: Debra J. Dorisio Deininger, Longmont, Colo.; Towner B. Scheffler, Butler, Pa.

[73] Assignee: Mine Safety Appliances Company, Pittsburgh, Pa.

[21] Appl. No.: 09/199,017

[22] Filed: Nov. 23, 1998

Related U.S. Application Data

[62] Division of application No. 08/887,025, Jul. 2, 1997.

[51] Int. Cl.[7] .................................................. G01N 27/404
[52] U.S. Cl. ......................... 204/412; 204/415; 204/431; 204/292; 205/780.5
[58] Field of Search ................................... 204/412, 415, 204/431, 432; 205/780.5, 782.5, 783

[56] References Cited

U.S. PATENT DOCUMENTS

| | | | |
|---|---|---|---|
| 2,912,367 | 11/1959 | Asendorf et al. | 205/780.5 |
| 3,354,069 | 11/1967 | Jerrold-Jones et al. | 204/435 |
| 3,470,071 | 9/1969 | Vertes et al. | 205/780.5 |
| 3,950,231 | 4/1976 | Frant et al. | 205/780.5 |
| 4,065,363 | 12/1977 | Herrmann | 205/780.5 |
| 4,172,770 | 10/1979 | Semersky et al. | 204/415 |
| 4,227,974 | 10/1980 | Petersen et al. | 204/412 |
| 4,522,690 | 6/1985 | Venkatasetty | 204/415 |
| 4,810,352 | 3/1989 | Bone et al. | 204/415 |

FOREIGN PATENT DOCUMENTS 0531745  8/1992  European Pat. Off.

*Primary Examiner*—T. Tung
*Attorney, Agent, or Firm*—James G. Uber; Henry E. Bartony, Jr.

[57] ABSTRACT

The present invention provides an electrochemical sensor for the detection of hydrogen cyanide. In general, the electrochemical sensor includes a housing having disposed therein a working electrode, a reference electrode and a counter electrode. The electrochemically active surfaces of the working electrode and reference electrode preferably comprise silver. Electrical connection is maintained between the working electrode and the counter electrode via an organic electrolyte present within the housing. The electrochemical gas sensor preferably further comprises circuitry for maintaining the working electrode at a potential in the range of approximately +40 mV to approximately –40 mV versus the silver reference electrode. Most preferably, the electrochemical gas sensor comprises circuitry for maintaining the working electrode at a potential of approximately 0 mV versus the silver reference electrode.

20 Claims, 4 Drawing Sheets

ELECTROCHEMICAL SENSOR FOR THE DETECTION OF HYDROGEN CYANIDE

RELATED APPLICATIONS

This is a divisional of U.S. Ser. No. 08/887,025 filed on Jul. 2, 1997.

FIELD OF THE INVENTION

The present invention relates to an electrochemical sensor, and particularly, to an electrochemical sensor for detecting hydrogen cyanide.

BACKGROUND OF THE INVENTION

In an electrochemical gas sensor, the gas to be measured typically passes from the atmosphere into the sensor housing through a gas porous or gas permeable membrane to a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working and counter electrodes. A comprehensive discussion of electrochemical gas sensors is also provided in Cao, Z. and Stetter, J. R., "The Properties and Applications of Amperometric Gas Sensors," *Electroanalysis,* 4(3), 253 (1992), the disclosure of which is incorporated herein by reference.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

Electrical connection between the working electrode and the counter electrode is maintained through an electrolyte. The primary functions of the electrolyte are: (1) to efficiently carry the ionic current; (2) to solubilize the analyte gas; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction reaction occurs to provide a mechanism whereby the ionic conduction of the electrolyte solution is coupled with the electron conduction of the electrode to provide a complete circuit for a current.

The measurable current arising from the cell reactions of the electrochemical cell is directly proportional to the rate of reaction. Preferably, therefore, a high reaction rate is maintained in the electrochemical cell. For this reason, the counter electrode and/or the working electrode of the electrochemical cell generally comprise an appropriate electrocatalyst on the surface thereof to enhance the reaction rate. If the reaction rate of either half cell reaction is impeded, resulting in a low exchange current density, the equilibrium current of the electrochemical cell may be easily perturbed during measurement. Such deviation can result in undesirable side reactions and/or nonlinear behavior over the range of analyte concentrations desired to be detected.

The type, rate, and efficiency of the chemical reactions within an electrochemical gas sensor are controlled, in significant part, by the material(s) used to make the working electrode and counter electrode. Indeed, extensive research efforts are expended to develop improved working electrodes, counter electrodes and electrochemical systems generally. See Cao, supra.

In the case of electrochemical sensors for the detection of hydrogen cyanide (HCN), these efforts have met with somewhat limited success. In that regard, currently available electrochemical sensors for the detection of HCN suffer from a number of significant drawbacks, including: (1) high base line current; (2) substantial and unpredictable sensitivity to changes in temperature; and (3) susceptibility to interference from or cross-sensitivity to gases other than HCN.

It is desirable, therefore, to develop new electrochemical sensors and electrodes for use in such electrochemical sensors for the detection of hydrogen cyanide which mitigate or substantially eliminate one or more of the above drawbacks.

SUMMARY OF THE INVENTION

The present invention provides an electrochemical sensor for the detection of hydrogen cyanide. In general, the electrochemical sensor preferably comprises a housing having disposed therein a working electrode, a reference electrode and a counter electrode. The electrochemically active surface of the working electrode preferably comprises silver. The electrochemically active surface of the reference electrode also preferably comprises silver. Electrical connection is preferably maintained between the working electrode and the counter electrode via an organic electrolyte present within the housing.

The electrochemical gas sensor preferably further comprises circuitry for maintaining the working electrode at a potential in the range of approximately +40 mV to approximately −40 mV versus the silver reference electrode (that is, the operating potential is preferable in the range of approximately −40 mV to approximately +40 mV relative to the silver reference electrode). More preferably, the working electrode is maintained at a potential in the range of approximately +20 mV to approximately −20 mV versus the silver reference electrode. Most preferably, the working electrode is maintained at a potential of approximately 0 mV versus the silver reference electrode.

Although the composition of the electrochemically active surface of the counter electrode can generally comprise any suitable material, the electrochemically active surface of the counter electrode preferably comprises silver.

The present invention also provides a method of using an electrochemical gas sensor comprising a working electrode having an electrochemically active surface comprising silver and a reference electrode having an electrochemically active surface comprising silver for the detection of hydrogen cyanide. The method preferably comprises the steps of:

a. placing the electrochemical gas sensor in communicative connection with an environment containing hydrogen cyanide such that hydrogen cyanide can react at the working electrode; and b. measuring the current flow between the working electrode and the counter electrode to obtain a measurement of the concentration of hydrogen cyanide in the environment.

The method preferably further comprises the step of:

c. maintaining the working electrode at a potential in the range of approximately +40 mV to approximately −40 mV versus the silver reference electrode.

DETAILED DESCRIPTION OF THE INVENTION

Figure 1:
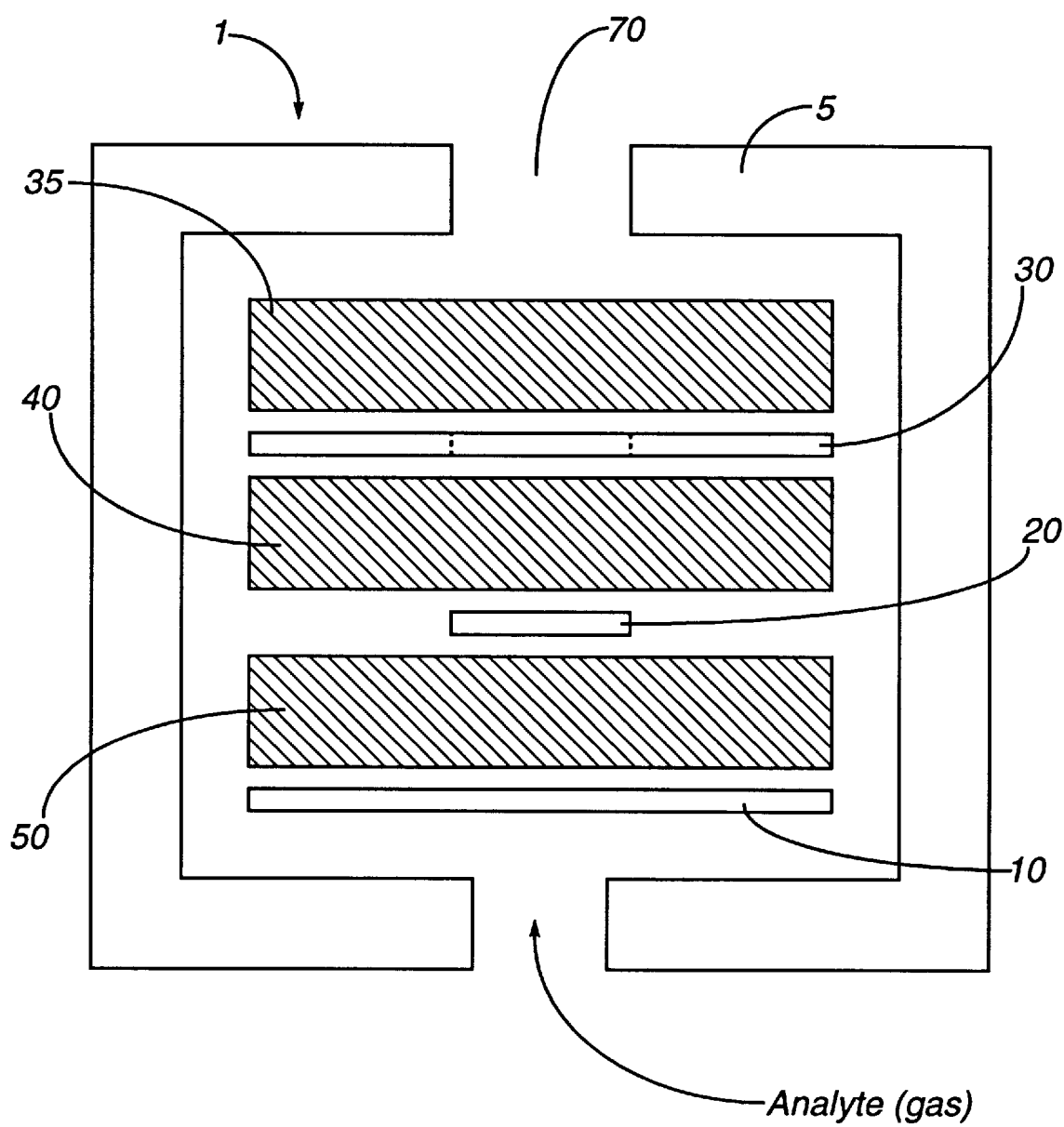
FIG. 1 illustrates a simplified schematic representation of a cross-sectional view of an embodiment of an electrochemical gas sensor of the present invention.

As seen in FIG. 1, electrochemical hydrogen cyanide sensor 1 preferably comprises a housing 5, enclosing a working electrode 10, a reference electrode 20 and a counter electrode 30. In fabricating electrochemical hydrogen cyanide sensors 1 for use in the present studies a porous spacer or wick 35 was first placed within housing 5. Counter electrode 30 was then placed into housing 5. A porous spacer or wick 40 was preferably then placed within housing 5 followed by reference electrode 20. A porous wick 50 was subsequently placed within housing 5 followed by working electrode 10. A detailed discussion of a preferred assembly, including connection of electrical leads, for electrochemical gas sensor 1 is set forth in U.S. Pat. No. 5,338,429, the disclosure of which is incorporated herein by reference.

After placement of working electrode 10 within housing 5, the perimeter of working electrode 10 was heat sealed to housing 5. The interior of housing 5 was then filled with an organic electrolyte via opening 70. Upon filling of the interior of housing 5 with electrolyte, opening 10 was sealed, preferably via heat sealing using a diffusion barrier through which gas is mobile but through which the organic electrolyte system is substantially immobile. An example of a diffusion barrier suitable for use in the present invention is a Zintex® film. Zintex is available from W. L. Gore and Associates, Inc. A detailed discussion of diffusion membranes preferred for use with organic electrolytes is set forth in U.S. patent application Ser. No. 08/617,504, entitled "Electrochemical Gas Sensor With a Non-Aqueous Electrolyte System," and filed Mar. 15, 1996, the disclosure of which is incorporated herein by reference.

Wicks 40 and 50 operate to prevent physical contact of the electrodes but allow the liquid electrolyte to contact the electrodes and thereby provide ionic connection between working electrode 10 and counter electrode 30. The electrolyte used in electrochemical hydrogen cyanide sensor 1 of the present studies was a solution of propylene carbonate, triethanolamine and tetraethylammonium perchlorate.

The electrochemically active surface of working electrode 10 preferably comprises silver (Ag). Working electrodes 10 for use in electrochemical sensors 1 for the present studies were preferably fabricated via deposition of an ink comprising silver metal powder and a dispersed Teflon® powder upon a Zintex membrane. The ink may be deposited via silk screening upon a Zintex film as known in the art in connection with deposition of electrochemically active materials upon GoreTex® films. Zintex films were found to provide a good support for the electrochemically active material. The ink may also be deposited using hand painting techniques as known in the art. Working electrodes 10 for the present studies were fabricated via silk screening. Reference electrodes 20 were also fabricated via silk screening a silver metal ink upon a Zintex membrane. Preferably, a film of electrochemically active material having a thickness in the range of approximately 1 mil to 10 mil (0.025 mm to 0.25 mm) is deposited upon the electrodes of the present invention.

Counter electrodes 30 for use in electrochemical sensors 1 for the present studies may also be fabricated via silk screen deposition of an ink comprising a suitable electrochemically active material. In general, the electrochemically active material used in counter electrodes 30 is not important. In a preferred embodiment, however, the electrochemically active surface of counter electrode 30 also comprises silver. In the case of silver, counter electrodes 30 for the present studies were preferably fabricated via silk screening deposition of an ink comprising silver powder and Teflon powder upon a Zintex membrane as discussed above for working electrode 10 and reference electrode 20.

After deposition of the films upon working electrode 10, reference electrode 20 and counter electrode 30 as described above, the films were preferably sintered to fix the electrochemically active material upon the substrate Zintex such as is described in U.S. Pat. No. 4,790,925 in connection with other substrate membranes, the disclosure of which is incorporated herein by reference.

Figure 2:
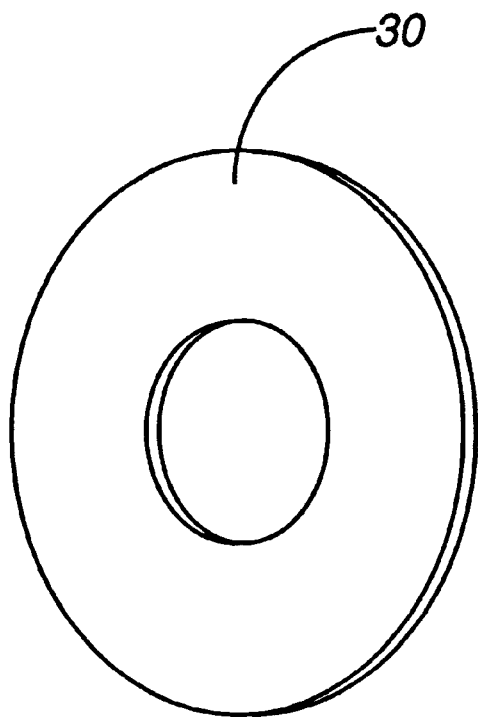
FIG. 2 illustrates a perspective view of an embodiment of the present counter electrode.
Figure 3:
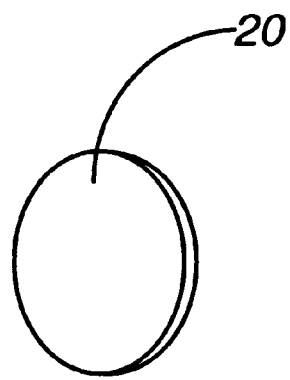
FIG. 3 illustrates a perspective view of an embodiment of the present reference electrode.

As illustrated in FIGS. 1 and 2, counter electrode 30 is preferably shaped in the general form of an annulus or ring. As illustrated in FIGS. 1 and 3, reference electrode 20 is preferably shaped in a generally circular form (that is, in the general shape of a disk). As clear to those skilled in the art, however, counter electrode 30, reference electrode 20 and working electrode 10 of electrochemical sensor 1 can be fabricated in many different shapes.

Preferably, working electrode 10, reference electrode 20 and counter electrode 30 are formed from a single membrane after sintering of the silver thereon. Forming working electrode 10, reference electrode 20 and counter electrode 30 from the same membrane minimizes surface differences between the electrodes and improves sensor performance. In the case of the electrodes of FIGS. 1 through 3, counter electrode 30 and reference electrode 20 can be fabricated simultaneously by simply stamping or cutting out disk-shaped reference electrode 20 from the center of a larger disk-shaped membrane, thereby simultaneously forming annular counter electrode 30.

Typically, electrochemical sensors are subjected to a "cook-dow" or "equilibration" period before use thereof to provide an adequately stable and low baseline current.

During the cook-down or equilibration period, the electrochemical sensor is stored at ambient conditions and maintained at operating potential for a defined period of time. As the most preferred operating potential of the hydrogen cyanide electrochemical sensor 1 is preferably approximately 0 mV versus the silver reference electrode, working electrode 10 is simply stored at a potential of approximately 0 mV versus silver reference electrode 20 by shorting together working electrode 10 and reference electrode 20 via an external shorting clip. A cook-down period is thus unnecessary. A substantially stable baseline current in the range of approximately −0.05 $\mu$A to approximately +0.05 $\mu$A was achieved with hydrogen cyanide electrochemical sensors 1.

Response time and response time ratio (RTR) are empirical measures of the speed of response of a sensor and are critically dependent on the manner in which the test is performed (for example, the length of time the experiment lasts and/or the time at which the sensor reaches 100% of its final output). In the present studies, both response time and RTR were based upon a ten (10) minute exposure to test gas. RTR was calculated by dividing (i) the sensor output after one (1) minute of exposure to hydrogen cyanide test gas by (ii) the sensor output after ten (10) minutes of exposure to hydrogen cyanide test gas. Based upon a ten-minute test, RTR is also the percentage of final response (that is, response or output obtained after ten minutes) obtained in one minute. Response time was generally tabulated as the 90% response time ($t_{90}$) unless otherwise indicated. The $t_{90}$ response time is the time, in seconds, required for the sensor to reach 90% of the response or output obtained after ten minutes of exposure to test gas. The sensitivity (in units of $\mu$A/ppm HCN) was established as the sensor output after ten (10) minutes of exposure to hydrogen cyanide.

The present studies were performed under computer control in which twenty (20) sensors could be tested simultaneously. A baseline current reading for each sensor was established as the sensor output after a ten-minute exposure to air (0 ppm hydrogen cyanide). In testing for hydrogen cyanide concentration, air was first applied to electrochemical sensors 1 for a period of time followed by application of air having a known concentration of hydrogen cyanide (for example, 15 ppm hydrogen cyanide) for a period of time.

All the sensor cells in the studies had a single 0.188 inch diameter inlet hole to allow the test gas to enter the sensor cells. An average output of approximately 0.13 $\mu$A/ppm was obtained under these experimental conditions. As is clear to one of ordinary skill in the art, sensitivity can generally be increased by increasing the total surface area of such inlet holes to allow more gas to enter the sensor cell. The electrochemical sensors of the present invention were found to provide a signal/noise ratio suitable to measure concentrations of hydrogen cyanide at least as low as 0.5 ppm.

The electrochemical sensors of the present invention were found to provide a substantially linear signal over at least the range of approximately 0 to 50 ppm hydrogen cyanide. Concentrations higher than 50 ppm were not studied, however. The response time of the present sensors was found to be less than approximately 10 seconds to 90%. An RTR of approximately 0.95 was found.

Figure 4:
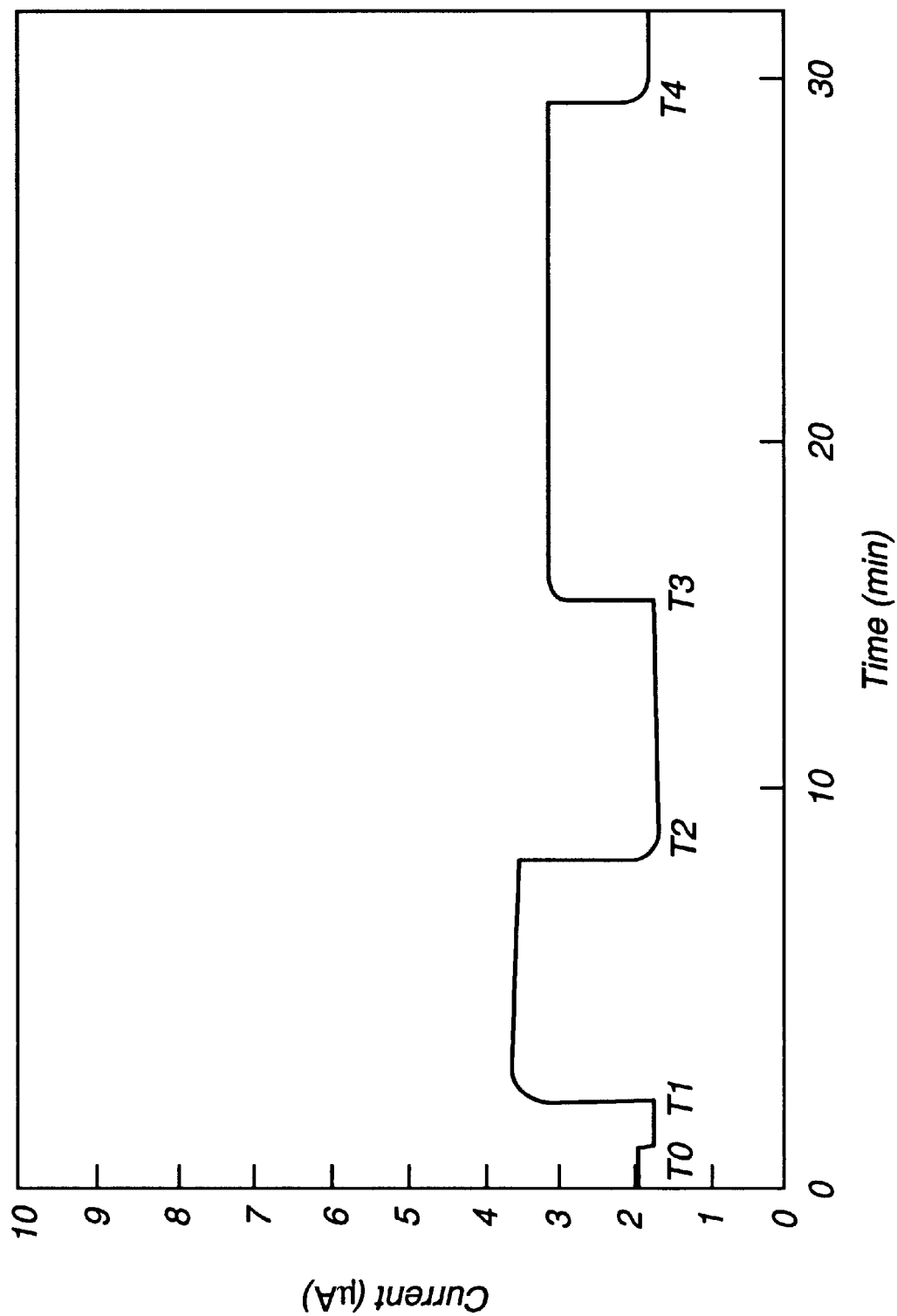
FIG. 4 illustrates the output of an electrochemical gas sensor of the present invention in the presence of hydrogen cyanide gas.

FIG. 4 illustrates the output of an electrochemical sensor of the present invention in the presence of hydrogen cyanide at an operating potential of 0 mV versus the silver reference electrode. The reference electrode and the working electrode were fabricated from relatively "low" specific surface area powdered silver having a particle size of 4 to 7 microns (available from ALFA-Ventron and having ALFA-Ventron Part Number 11402). In the study of FIG. 4, the electrochemical sensor was exposed to an air sample gas. At time T1 a concentration of approximately 11 ppm hydrogen cyanide was introduced into the sample gas. The hydrogen cyanide supply was discontinued at time T2. A concentration of approximately 8 ppm hydrogen cyanide was introduced into the sample gas at time T3 and was later discontinued at time T4.

Figure 5:
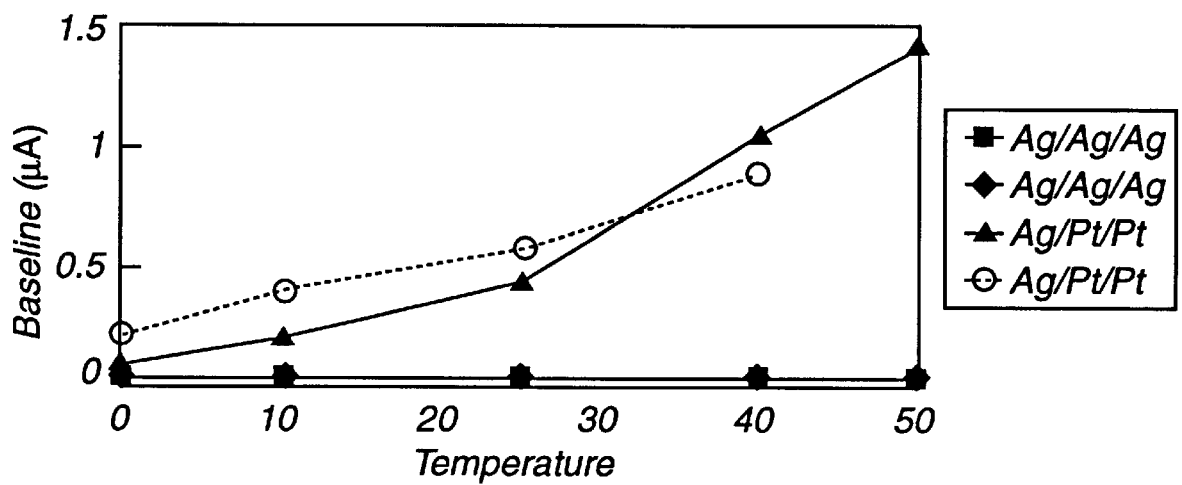
FIG. 5 illustrates a comparison between the baseline current of an electrochemical gas sensor of the present invention and that of an electrochemical sensor comprising a silver working electrode, a platinum reference electrode and a platinum counter electrode as a function of temperature.

Unlike currently available sensors for the detection of hydrogen cyanide, however, the sensors of the present invention were found to be relatively insensitive to changes in temperature. In that regard, previous hydrogen cyanide sensors exhibit an immediate change in sensor output as a result of changes in temperature. In FIG. 5, the output of two electrochemical gas sensors of the present invention, in which the electrochemically active surface of each of the working electrode, reference electrode and counter electrode comprises silver (Ag/Ag/Ag), is compared to two electrochemical gas sensors in which the electrochemically active surface of the working electrode comprises silver and the electrochemically active surface of each of the reference electrode and counter electrode comprises platinum (Ag/Pt/Pt).

The results of several interferent studies are set forth in Table 1 below. The data provided for each interferent gas correspond to the sensor output (that is, the indicated concentration of hydrogen cyanide in ppm) upon exposure of the sensor to 10 ppm of the interferent gas. The results indicate that the present sensor is less susceptible to erroneous results arising from the presence of the interferent gases studied than previous hydrogen cyanide sensors.

Although the present invention has been described in detail in connection with the above examples, it is to be understood that such detail is solely for that purpose and that variations can be made by those skilled in the art without departing from the spirit of the invention except as it may be limited by the following claims.

TABLE 1

| Sample (10 ppm) | HCN | HCl | SO$_2$ | Cl$_2$ | CO | NO | NO$_2$ |
|---|---|---|---|---|---|---|---|
| Sensor Response (ppm HCN Indicated) | 10 | −.2 | .4 | −.3 | 0 | 0 | −.4 |

| Sample (10 ppm) | Toluene | H$_2$S | Ethylene | H$_2$ | NH$_4$ | CH$_4$ | EtOH |
|---|---|---|---|---|---|---|---|
| Sensor Response (ppm HCN Indicated) | 0 | .4 | 0 | 0 | 0 | 0 | .1 |

What is claimed is:

1. An electrochemical sensor for the detection of hydrogen cyanide, comprising: a housing, the housing having disposed therein a working electrode, a reference electrode and a counter electrode, the electrochemically active surface of the working electrode comprising silver, the electrochemically active surface of the reference electrode comprising sintered silver metal powder, electrical connection being maintained between the working electrode and the counter electrode via an organic electrolyte present within the housing.

2. The electrochemical gas sensor of claim 1 further comprising circuitry for maintaining the working electrode at a potential in the range of approximately +40 mV to approximately −40 mV versus the silver reference electrode.

3. The electrochemical sensor of claim 2 wherein the circuitry maintains the working electrode at a potential in the range of approximately +20 mV to approximately −20 mV versus the silver reference electrode.

4. The electrochemical sensor of claim 3 wherein the circuitry maintains the working electrode at a potential of approximately 0 mV versus the silver reference electrode.

5. The electrochemical sensor of claim 1 wherein the electrochemically active surface of the counter electrode comprises silver.

6. The electrochemical sensor of claim 5 wherein the counter electrode comprises sintered silver metal powder.

7. The electrochemical sensor of claim 6 wherein the electrolyte comprises a solution of propylene carbonate, triethanolamine and tetraethylammonium perchlorate.

8. The electrochemical sensor of claim 1 wherein the electrolyte comprises a solution of propylene carbonate, triethanolamine and tetraethylammonium perchlorate.

9. An electrochemical sensor for the detection of hydrogen cyanide, comprising: a housing, the housing having disposed therein a working electrode, a reference electrode and a counter electrode, the electrochemically active surface of the working electrode comprising sintered silver metal powder, the electrochemically active surface of the reference electrode comprising sintered silver metal powder, electrical connection being maintained between the working electrode and the counter electrode via an organic electrolyte present within the housing.

10. The electrochemical sensor of claim 9 wherein the electrolyte comprises a solution of propylene carbonate, triethanolamine and tetraethylammonium perchlorate.

11. The electrochemical gas sensor of claim 10 further comprising circuitry for maintaining the working electrode at a potential in the range of approximately +40 mV to approximately −40 mV versus the silver reference electrode.

12. The electrochemical sensor of claim 11 wherein the circuitry maintains the working electrode at a potential in the range of approximately +20 mV to approximately −20 mV versus the silver reference electrode.

13. The electrochemical sensor of claim 12 wherein the circuitry maintains the working electrode at a potential of approximately 0 mV versus the silver reference electrode.

14. The electrochemical sensor of claim 9 wherein the electrochemically active surface of the counter electrode comprises silver.

15. The electrochemical sensor of claim 14 wherein the electrolyte comprises a solution of propylene carbonate, triethanolamine and tetraethylammonium perchlorate.

16. The electrochemical sensor of claim 12 wherein the counter electrode comprises sintered silver metal powder.

17. The electrochemical gas sensor of claim 16 further comprising circuitry for maintaining the working electrode at a potential in the range of approximately +40 mV to approximately −40 mV versus the silver reference electrode.

18. The electrochemical sensor of claim 17 wherein the circuitry maintains the working electrode at a potential in the range of approximately +20 mV to approximately −20 mV versus the silver reference electrode.

19. The electrochemical sensor of claim 18 wherein the circuitry maintains the working electrode at a potential of approximately 0 mV versus the silver reference electrode.

20. The electrochemical sensor of claim 16 wherein the electrolyte comprises a solution of propylene carbonate, triethanolamine and tetraethylammonium perchlorate.

* * * * *